(12) United States Patent
Nakata et al.

(10) Patent No.: US 6,451,787 B1
(45) Date of Patent: Sep. 17, 2002

(54) REMEDIES FOR OCULAR DISEASES

(75) Inventors: Katsuhiko Nakata, Sakurai; Masaaki Kageyama, Neyagawa, both of (JP)

(73) Assignees: Cephalon, Inc., West Chester, PA (US); Kyowa Hakko Kogyo Co., Ltd. (JP)

( * ) Notice: Subject to any disclaimer, the term of this patent is extended or adjusted under 35 U.S.C. 154(b) by 0 days.

(21) Appl. No.: 09/807,293

(22) PCT Filed: Oct. 12, 1999

(86) PCT No.: PCT/JP99/05605
§ 371 (c)(1),
(2), (4) Date: Jun. 11, 2001

(87) PCT Pub. No.: WO00/21531
PCT Pub. Date: Apr. 20, 2000

(30) Foreign Application Priority Data

Oct. 13, 1998 (JP) ............................................. 10-290194

(51) Int. Cl.[7] .......................... A61K 31/19; A61K 31/40

(52) U.S. Cl. ................................... 514/211.08; 540/545

(58) Field of Search ...................... 540/545; 514/211.08

(56) References Cited

U.S. PATENT DOCUMENTS 6,200,968 B1 * 3/2001 Dickason et al. ...... 514/211.09

FOREIGN PATENT DOCUMENTS

| JP | 8-501080 | * | 2/1996 |
| WO | WO 94/02488 | | 2/1994 |
| WO | WO 97/30701 | | 8/1997 |
| WO | WO 97/49406 | | 12/1997 |

OTHER PUBLICATIONS

Naash M.L. et al., "Light–induced acceleration of photoreceptor degeneration in transgenic mice expressing mutant rhodospin", *Investigative Opthalmology & Visual Science,* 1996, 37(5), pp. 775–782.
Adachi, M. et al., "High intraocular pressure–induced ischemia and reperfusion injury in the optic nerve and retina in rats", *Graefe's Arch Clin Exp Ophtalmol.,* 1996, 234, pp 445–451.
Portera–Cailliau. C. et al., "Apoptotic photoreceptor cell death in mouse models of retinitis pigmentosa", *Proc Natl. Acad Sci, USA,* 1994, vol. 113, pp 880–886.
Jong–Chang, Chen et al., "Apoptotic photoreceptor cell death after traumatic retinal detachment in humans"., *Arch Ophthalmol,* 1995, vol. 113, pp 880–886.
Ganka, 1998, vol. 40 (3), pp 251–273 (*) No English language abstract available.
Lam T.T. et al., "The effect of aurintricarboxylic acid, an endonuclease inhibitor, on ischemia/reperfusion damage in rat retina", 1995, vol. 11 (3), pp 253–259.
Maroney, Anna C. et al., "Motoneuron apoptosis is blocked by CEP–1347 (KT 7515), a novel inhibitor of the JNK signaling pathway"., *The Journal of Neuroscience.,* 1998, 18(1), pp 104–111.
Perez Thereza R. M. et al., "DNA fragmentation characteristic of apoptosis and cell loss induced by kainic acid in rabbity retinas"., *Neurochem. Int.,* 1997, vol. 31, No. 2, pp 251–260.
Quigley, Harry A. et al., "Retinal ganglion cell death in experimntal glaucoma and after axotomy occurs by apoptosis", *Invest Opht & Visual Sci.,* 1995, vol. 36, No. 5, pp774–786.
Tapley, P. et al., "K252a is a selctive inhibitor of the tyrosine protein kinase activity of the trk family of oncogenes and neurotrophin receptors", *Oncogene,* 1992, 7, pp 371–381.
Tso, M.. O. M. et al., "Apoptosis leads to photoreceptor degeneration in inherited retinal dystrophy of rcs rats", 1994, vol. 35 (6), pp 2693–2699.
Unoki, K. et al., "Protection of the rat retina from ischemic injury by brain–derived neurotrophic factor, ciliary neurotrophic factor, and basic fibroblast growth factor", *Invet Opht & Visual Sci,* 1994, vol. 35, No. 3, pp 907–915.
Valenzuela, Garcia E., et al., "Programmed cell death of retinal ganglion cells during experimental glaucoma", *Exp Eye Res,* 1995, 61, pp 33–44.
*Graefes Arch. Clin. Exp.Ophthalmol.,* 1996, 234, S 209–213.
Robertson, G.S. et al., "Neuroprotective effects of K252a in cerebral ischemia: The NAIP Connection", *Society for Neuroscience Abstracts, Society for Neuroscience,* 1996, 22(1–3), 1667, XP 000990362.

* cited by examiner

*Primary Examiner*—Bruck Kifle
(74) *Attorney, Agent, or Firm*—Woodcock Washburn LLP

(57) ABSTRACT

Use of the compound represented by general formula (I) for remedies of and protection against eye diseases is disclosed. General formula (I):

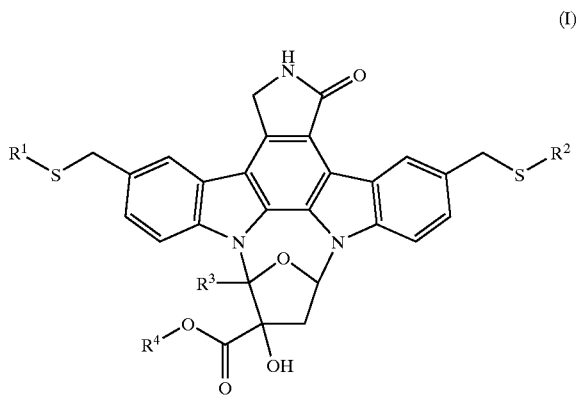

(wherein, $R^1$ and $R^2$ independently represent a lower alkyl group, $R^3$ and $R^4$ independently represent a hydrogen atom or a lower alkyl group).

7 Claims, No Drawings

REMEDIES FOR OCULAR DISEASES

CROSS-REFERENCE TO RELATED APPLICATIONS

This application is the U.S. national phase of International Application No. PCT/JP99/05605 filed Oct. 12, 1999, which claims priority to Japanese Application No. 10/290194 filed Oct. 13, 1998, each of which is incorporated herein by reference in its entirety.

BACKGROUND ART

The retina has a function to receive lights from outside and plays an important role in optic functions. It has a structure consisting of ten layers including the pigment layer of the retina, the inner plexiform layer, the layer of gangliocyte, the layer of nerve fiber and the like to form a tissue with the depth of 0.1–0.5 mm The inner plexiform layer contains neurocyte called amacrine cell which forms synapse in combination with gangliocytic process. This neurocyte is thought to act as a light detector since it shows superior responses at the starting point and the terminating point of irradiation of lights. The layer of gangliocyte contains neurocytes which bodies lie in the inner deepest part of the retina and deeply relates to movement vision, periscope, color perception, form perception and the like. Moreover, the blood vessels of the retina, that are the bifurcated blood vessels originated from the central retinal arteries and veins, run in the layer of nerve fiber and play a role to supply oxygen and nutrient with the optic nerve.

Recently, a notion of so-called "neuro-protection" becomes popular, which says that since in the case of glaucoma, disorders in retina circulation and axonal transport in the retinal nerve ultimately lead to dropping out of nerve fiber caused by death of gangliocytes, promoting the disease to visual field disturbance, developing a way of treatment to prevent or minimize death of gangliocyte will lead to an ultimate treatment of glaucoma (GANKA, 40, 251–273 (1998)). Actually, the papers have been publicized which show that disorders of the layer of retinal gangliocyte and the optic disc were observed even 45 minutes after ischemia in ischemic rats with ocular hypertension (Graefes Arch. Clin. Exp. Ophthalmol., 234, 445–451 (1996)) and that in rabbits with methyl cellulose-triggered ocular hypertension the density of retinal gangliocyte significantly decreased and the density of glia cell significantly increased after the rabbits had suffered from ocular hypertension for 10 days, and that then it was confirmed that there was a correlation between the extend of dropping out of gangliocyte and the size of the cell (Graefes Arch. Clin. Exp. Ophthalmol., 234, S209–S213 (1996)).

When vascular occlusion or hematostenosis occurs in the blood vessels of the retina by an element such as convulsion, clot, embolus, arterial sclerosis and the like, retina circulation is disturbed and supply of oxygen and nutrient to the retina or the optic nerve is blocked. Circulatory disturbance of the retina occupies an especially important position among retinal diseases. Representative examples of the conditions accompanied by circulation disturbance of the retina are retinal vascular occlusion in which the retinal veins or the retinal arteries cause occlusion or stenosis, diabetic retinopathy in which even detachment of the retina likely occurs, and ischemic optic neuropathy in which disorders of optic functions appear. Moreover, due to this circulatory disturbance of the retina, supply of oxygen or nutrient becomes insufficient, leading to death of retinal neurocytes. This death of retinal neurocytes is thought to deeply participate in some hereditary retinal diseases such as macular degeneration, pigmentary retinal dystrophy, Leber's disease and the like.

And it has been elucidated that apoptosis, that is one form of programmed cell death, shall participate in various forms of thology of eye diseases. For example, the fact that apoptosis occurs in retinal neurocytes is reported in the cases of retinal disorders caused by ischemia—reperfusion (J. Ocul. Pharmacol. Ther., 11, 253–259 (1995)), detachment of the retina (Arc. Ophthalmol., 113, 880–886 (1995)), retinal degeneration (Proc. Natl. Acad. Sci. USA, 91, 974–978 (1994), Invest. Ophthalmol. Vis. Sci., 35, 2693–2699 (1994)), light-induced retinal degeneration (Invest. Ophthalmol. Vis. Sci., 37, 775–782 (1996)), glaucoma (Invest. Ophthalmol. Vis. Sci., 36, 774–786 (1995), Exp. Eye Res., 61, 33–44 (1995)) and the like. That is, although there are various causes, it is highly possible that the resulting disorder in optic functions is caused by apoptosis occurring in neurocytes which construct an information network for optic perception.

Then, if there is a drug which has an effect to protect retinal gangliocyte, it is expected to be effective for the treatment of retinal diseases represented by retinal vascular occlusion, diabetic retinopathy, ischemic optic neuropathy, macular degeneration, pigmentary retinal dystrophy, Leber's disease as well as eye diseases such as glaucoma and the like.

On the other hand, International Patent Application WO 94/02488 discloses K-252a derivatives having a strong effect to promote choline acetyl transferase activity of the spinal cord and being effective for treatments of neurocytic degeneration such as Alzheimer's disease, amyotrophic lateral sclerosis (ALS), Parkinson's disease, cerebral ischemia and the like. Moreover, there are also other reports showing that these derivatives suppress apoptosis by the motor neuron (J. Neurosci., 18, 104–111 (1998)) and that these derivatives suppress over-production of tumor necrosis factor—α and interleukin—1β (in a brochure for International Patent Application WO 97/49406).

However, no report has been publicized which studies these derivatives in ophthalmologic field.

DISCLOSURE OF THE INVENTION

It has been very interesting challenge to find out therapeutic agents for retinal diseases represented by retinal vascular occlusion, diabetic retinopathy, ischemic optic neuropathy, macular degeneration, pigmentary retinal dystrophy, Leber's disease as well as eye diseases such as glaucoma and the like which have peculiar characteristics in their action mechanisms.

As the inventors put their focus on known drugs used as therapeutic agents for degeneration of neurocyte from the view point of nerve protection and investigated the effects thereof on retinal gangliocyte, it was confirmed that K-252a derivatives protect retinal neurocyte from disorders and it was found that the derivatives are effective as therapeutic agents for retinal diseases represented by retinal vascular occlusion, diabetic retinopathy, ischemic optic neuropathy, macular degeneration, pigmentary retinal dystrophy, Leber's disease as well as other eye diseases such as glaucoma and the like.

The invention relates to use of K-252a derivatives (it is referred to as the compounds hereinafter) represented by the following general formula (I) for therapeutic agents of optical diseases such as therapeutic agents of glaucoma, therapeutic agents of retinal diseases or the like as well as for remedies of the said diseases.

General Formula (I):

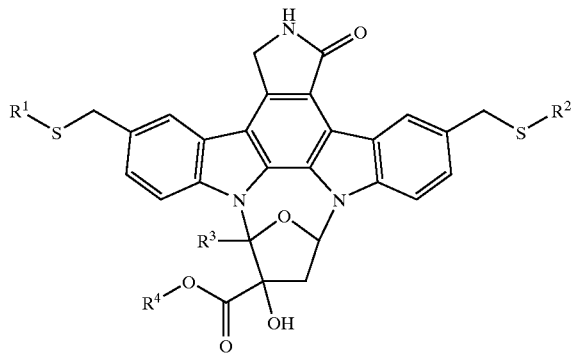

(I)

wherein, $R^1$ represents a lower alkyl group, $R^2$ represents a lower alkyl group, $R^3$ represents a hydrogen atom or a lower alkyl group, and $R^4$ represents a hydrogen atom or a lower alkyl group More specifically, according to the invention, medical formulations to treat or prevent eye diseases are provided, which comprise the compound represented by general formula (I) in an amount effective to treat or prevent the eye diseases, as well as vehicles or additives.

As another embodiment of the invention, remedies or preventive methods comprising administering to a patient which needs a remedy or prevention of an eye disease the compound represented by general formula (I) in an amount sufficient to the said remedy or prevention are provided.

As further embodiment of the invention, use of the compound represented by general formula (I) as an active ingredient contained in a medical formulation to treat or prevent an eye disease is provided.

BEST MODE FOR CARRYING OUT THE INVENTION

In the context of the invention, the lower alkyl means straight or branched alkyl with 1–6 carbon atom(s) such as methyl ethyl, propyl, butyl, hexyl, isopropyl, isobutyl, tert-butyl or the like.

As a preferable example of the compound, a compound in which both $R^1$ and $R^2$ represent an ethyl group and both $R^3$ and $R^4$ represent a methyl group can be mentioned (it is referred to as Compoud A hereinafter), with the specified structure of the most preferable example represented by the following formula (II).

Formula (II):

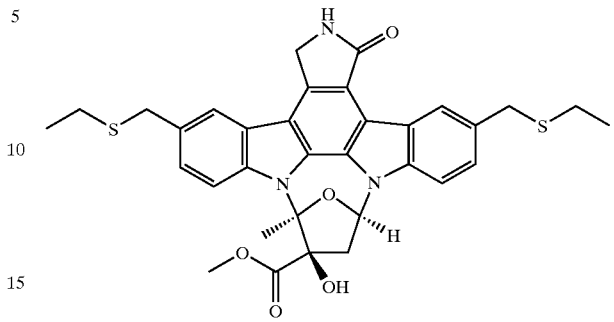

(II)

Whereas the detailed effects of the compounds on retinal neurocytes will be explained in the section of Pharmacological Tests described hereinafter, it was confirmed that the compounds suppress the decline in the number of the cells in the layer of retinal ganglyocyte when the above-descrived effects were examined using the retina subjected to an ischemia—reperfusion treatment and the eyes treated with kainic acid.

The route of administration of the compounds can be either parenteral or oral. As dosage forms for parenteral administration, eye drop, injection, nose drop and the like can be mentioned whereas as for oral administration, tablet, capsule, powder and the like can be mentioned, all of which can be formulated using vehicles or additives as well as techniques routinely used in the art. For example, in the case of an eye drop, as the vehicles or additives, isotonizing agents such as sodium chloride, concentrated glycerin and the like, buffering agents such as sodium phosphate, sodium acetate and the like, surfactants such as polyoxyethylene sorbitan mono-oleate (it is referred to as Polysorbate 80 hereinafter), polyoxyl stearate 40, polyoxyethylene hydrogenated castor oil and the like, stabilization agents such as sodium citrate, sodium edetate and the like, as well as preservatives such as benzalkonium chloride, parabens and the like can be used when required to formulate the composition, and pH of the formulation should be within the range acceptable to ophthalmologic formulations with the range of pH 4–8 being preferable.

The dose can be suitably selected depending on the conditions and age of the patient, dosage form and the like, and in the case of eye drops, it is appropriate to administer an eye drop of 0.01–10% (w/v) once or a couple of times a day and in the case of injections, it is usually appropriate to administer 0.0001–1 mg of the compound once a day or in divided doses. Moreover, in the case of oral drugs, it may be usually appropriate to administer 10 $\mu$g–1 g of the compound once a day or in divided doses.

The results from the Pharmacological Tests are illustrated hereinafter, but it should be understood that these examples are intended for better understanding of the invention and are not to limit the extent of the invention.

EXAMPLES

Pharmacological Tests

In order to study usefulness of the compounds, the effects of the compounds on the retina subjected to the ischemia—reperfusion treatment and on the retina from the eyes treated with kainic acid were examined.

1. Effects on the Retina Subjected to the Ischemia—Reperfusion Treatment

It has been reported that brain-derived neurotrophic factor (it is referred to as BDNF hereinafter) which is a neurotrophic factor has a protective effect against gangliocytic death caused by retinal ischemia (Invest. Ophthalmol. Vis. Sci. 35, 907–915 (1994)).

Thus, according to the method described in this reference, the effects of the compounds on retinal gangliocyte in a retinal ischemia—reperfusion model were studied.

Method of Experiment

Under anesthesia with a mixture of Ketalar and Celactal, the conjunctiva of a male Spraugue—Dawley rat (300–450 g) was dissected to expose the optic nerve and then the retina was subjected to an ischemic state by ligating the optic nerve with a suture. Sixty minutes after the ischemia, the suture was taken out to reperfuse the retina with the blood by allowing the circulation. Seven days after the reperfusion, the eye bulb was enucleated and then immobilized with paraformaldehyde, and after embedding it in paraffin, the transverse paraffin sections of the eye bulb with 3 $\mu$m of the thickness were prepared by slicing the eye bulb beginning from the point of exposure of the optic nerve with 60 $\mu$m of each interval. These sections were stained with hematoxylin—eosin and photographs were taken for the section in which the retinal part at the distance of approximately 1 mm from the optic disc to either direction, left or right, is included to measure the number of the cells contained in the layer of gangliocyte.

Here, the compound was dissolved into polyethylene glycol 660 hydroxystearate and injected in the volume of 1 $\mu$l into the hyaloid body two day before the creation of the ischemic state.

Results

In Table 1, as one example of the experimental results, the number of the cells in the layer of gangliocyte in the case in which a solution of Compound A prepared at the concentration of 3 mg/ml was injected (the amount injected: 3 $\mu$g/eye) is shown. Also, the results from the experiments in which neither of the ischemia—reperfusion treatment nor the injection of the compound was conducted (it is referred to as Normal Group (1) hereinafter) as well as those in which the ischemia—reperfusion treatment was conducted 30 and then only polyethylene glycol 660 hydroxystearate without the compound was injected (it is referred to as Control Group (1) herein-after) are shown.

TABLE 1

|  | Number of the cells in the layer of gangliocyte (cells/mm) |
| --- | --- |
| Normal Group (1) (5) | 38.8 |
| Control Group (1) (7) | 20.5 |
| Group with the injection of Compound A (3 $\mu$g/eye) (10) | 27.5 |

Note: The figures in the table show the averages for the cases studied, the numbers of which are indicated within the right parentheses.

As shown in Table 1, when 3 $\mu$g of compound A was injected, it was confirmed that the compound suppressed the decline in the number of the cells in the layer of gangliocyte caused by the ischemia—reperfusion treatment and the number of the cells was recovered to the level of 70.9 % of that for Normal Group (1).

From this fact, Compound A was proved to have a superior protective effect on neurocyte disturbance of the retina caused by the ischemia—reperfusion treatment.

2. Effects on the Retina From the Eye Treated with Kainic Acid

It has been reported that when kainic acid, that is a neurotoxin, is injected into the hyaloid body, the inner plexiform layer becomes thinner because of synaptic collapse caused by cell death of amacrine cell or the number of the cells contained in the layer of gangliocyte decreases because of apoptosis happening to those cells (Neurochem. Int., 31, 251–260 (1997)).

Then, according to the method described in this reference, the effects of the compound on the retinal disturbance induced by injecting kainic acid into the hyaloid body were studied.

Method of Experiment

To a male Sprague—Dawley rat (180–250 g) under anesthesia with pentobarbital, a solution of kainic acid in polyethylene glycol 660 hydroxystearate (1 mmol/L) was injected into the hyaloid bodies in both of the eyes in the amount of 5 $\mu$l under observation with a stereoscopic microscopy. Seven days after the kainic acid treatment, the eye bulbs were enucleated, and immobilized with glutaraldehyde—paraformaldehyde, and after embedding them in paraffin, the transverse paraffin sections of the eye bulbs with 3 $\mu$m of the thickness were prepared by slicing the eye bulbs beginning from the point of exposure of the optic nerve with 60 $\mu$m of each interval. These sections were stained with hematoxylin—eosin and photographs were taken for the sections in which the retinal part at the distance of approximately 1 mm from the optic disc to either direction, left or right, is included to measure the thickness of the inner plexiform layer and the number of the cells contained in the layer of gangliocyte.

The compound was dissolved into polyethylene glycol 660 hydroxystearate and then injected into the hyaloid bodies two days before, at the same time as and one day after the kainic acid treatment in the volume of 5 $\mu$l each.

Results

In Table 2, as examples of the results from the experiments, the thickness of the inner plexiform layer and the numbers of the cells in the layer of gangliocyte for the cases in which a solution of Compound A prepared at the concentration of 6 $\mu$l (the amount injected: 30 ng/eye) and of 600 $\mu$g/ml (the amount injected: 3 $\mu$g/eye) were injected are shown. Also, the results from the experiments in which neither the treatment with kainic acid nor the injection of the compound was conducted, but only the injection of polyethylene glycol 660 hydroxystearate was conducted (it is referred to as Normal Group (2) hereinafter), as well as those in which the treatment with kainic acid was conducted, and only polyethylene glycol 660 hydroxystearate without the compound was injected (it is referred to as Control Group (2) hereinafter) are shown.

TABLE 2

|  | Thickness of the inner plexiform layer ($\mu$m) | Number of the cells in the layer of gangliocyte (cells/mm) |
| --- | --- | --- |
| Normal Group (2) | 47.5 | 64.2 |
| Control Group (2) | 20.8 | 36.8 |
| Group with the injection of Compound A (30 $\mu$g/eye) | 23.8 | 42.3 |

TABLE 2-continued

| | Thickness of the inner plexiform layer (μm) | Number of the cells in the layer of gangliocyte (cells/mm) |
|---|---|---|
| Group with the injection of Compound A (3 μg/eye) | 28.8 | 51.8 |

Note: The figures contained in the table show the averages of the five eyes studied.

As shown in Table 2, when 3 μg of Compound A was injected, thinning propensity of the inner plexiform layer and the decline in the number of the cells in the layer of gangliocyte caused by kainic acid were suppressed. Especially, for the number of the cells in the layer of gangliocyte, the cell number was confirmed to be recovered to the level of 80.7% of that for Normal group (2).

From this fact, Compound A was proved to have a superior protective effect against neurocyte disturbance of the retina caused by the kainic acid treatment.

Industrial Applicability

The compound was found to protect the retina against neurocyte disturbance of the retina subjected to the ischemia—reperfusion treatment and the kainic acid treatment as well as be effective as a therapeutic agent for retinal diseases represented by retinal vascular occlusion, diabetic retinopathy, ischemic optic neuropathy, macular degeneration, pigmentary retinal dystrophy, Leber's disease as well as other eye diseases such as glaucoma and the like.

Therefore, the invention has an applicability in drug manufacturing industry or health care industry.

What is claimed is:

1. A method of treating an eye disease in a human comprising administering to said human a compound of the formula

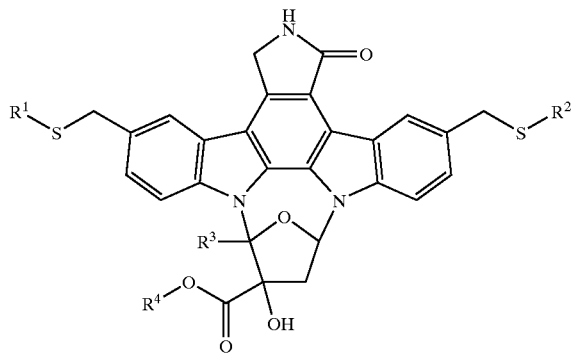

wherein, $R^1$ represents a lower alkyl group, $R^2$ represents a lower alkyl group, $R^3$ represents a hydrogen atom or a lower alkyl group, and $R^4$ represents a hydrogen atom or a lower alkyl group;

wherein said eye disease is pigmentary retinal dystrophy, Leber's disease, ischemic optic neuropathy, or retinal vascular occlusion.

2. The method of claim 1 wherein both $R^1$ and $R^2$ represent an ethyl group and both $R^3$ and $R^4$ represent a methyl group.

3. The method of claim 1 wherein said eye disease pigmentary retinal dystrophy.

4. The method of claim 1 wherein said eye disease is Laber's disease.

5. The method of claim 1 wherein said eye disease is retinal vascular occlusion or ischemic optic neuropathy.

6. A method of decreasing death of retinal gangliocytes in a human comprising administering to said human a compound of the formula

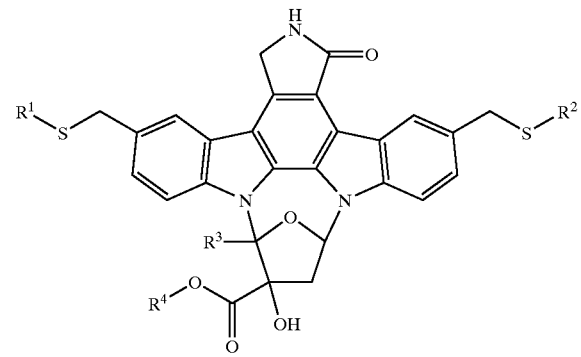

wherein, $R^1$ represents a lower alkyl group, $R^2$ represents a lower alkyl group, $R^3$ represents a hydrogen atom or a lower alkyl group, and $R^4$ represents a hydrogen atom or a lower alkyl group.

7. The method of claim 6 wherein both $R^1$ and $R^2$ represent an ethyl group and both $R^3$ and $R^4$ represent a methyl group.

* * * * *

UNITED STATES PATENT AND TRADEMARK OFFICE
CERTIFICATE OF CORRECTION

PATENT NO. : 6,451,787 B1
DATED : September 17, 2002
INVENTOR(S) : Katsuhiko Nakata and Masaaki Kageyama It is certified that error appears in the above-identified patent and that said Letters Patent is hereby corrected as shown below:

Title page, Item [54] and Column 1, line 1,
Title, please delete "REMEDIES FOR OCULAR DISEASES" and insert
-- AN AGENT FOR TREATING OPHTHALMOPATHY -- therefor.

Title page,
Item [56], References Cited, OTHER PUBLICATIONS, "Portera-Cailliau et al.," reference, please delete "vol. 113, pp. 880-886 and insert -- vol. 91, pp 974-978 -- therefor.
"Perez Thereza R.M. et al.," reference, please delete "rabbity" and insert -- rabbit --
"Quigley, Harry A. et al.," reference, please delete "experimntal" and insert
-- experimental -- therefor.
"Tapley, P. et al.," reference, please delete "selctive" and insert -- selective -- therefor.

Column 1,
Line 10, please insert the following paragraph
"The invention relates to therapeutic preparations of K-252a derivatives for eye diseases and use thereof for treatments of eye diseases."

Column 4,
Line 23, plesae delete "ganglyocyte" and insert -- gangliocyte" and delete "above-descrived" and insert -- above-described -- therefor.

Column 5,
Line 44, please delete "30".

Column 6,
Line 45, please delete "30 ng/eye" and insert -- 30 $\mu$g/eye -- therefor.

UNITED STATES PATENT AND TRADEMARK OFFICE
CERTIFICATE OF CORRECTION

PATENT NO.    : 6,451,787 B1
DATED         : September 17, 2002
INVENTOR(S)   : Katsuhiko Nakata and Masaaki Kageyama It is certified that error appears in the above-identified patent and that said Letters Patent is hereby corrected as shown below:

Column 8,
Line 20, please delete "Laber's" and insert -- Leber's -- therefor.

Signed and Sealed this

Fourth Day of January, 2005

JON W. DUDAS
*Director of the United States Patent and Trademark Office*